United States Patent [19]
Crew

[11] 4,151,838
[45] May 1, 1979

[54] INTERNAL MAMMARY ARTERY STERNAL RETRACTOR

[76] Inventor: John R. Crew, 255 Moncada Way, San Francisco, Calif. 94127

[21] Appl. No.: 807,679

[22] Filed: Jun. 17, 1977

[51] Int. Cl.² ............................................. A61B 17/02
[52] U.S. Cl. .................... 128/20; 128/303 R
[58] Field of Search ........................ 128/3, 12, 15, 341, 128/303 R, 20, 323, 361, 324, 352, 353; 254/131; D8/40, 18

[56] References Cited

U.S. PATENT DOCUMENTS

| | | | |
|---|---|---|---|
| 1,185,292 | 5/1916 | Dean | 128/20 |
| 1,309,734 | 7/1919 | Hemfling | 254/131 |
| 1,389,820 | 9/1921 | Downey | 254/131 |
| 1,530,946 | 3/1925 | Johnson | 254/131 |
| 2,653,006 | 9/1953 | Lewis | 254/131 |
| 2,896,910 | 7/1959 | Cooper et al. | 254/131 |
| 3,731,673 | 5/1973 | Halloran | 128/20 |
| 3,985,338 | 10/1976 | Herrmann | 254/131 |

FOREIGN PATENT DOCUMENTS 320796 10/1929 United Kingdom ..................... 254/131

OTHER PUBLICATIONS

*General Operating Instruments* from Holco Catalog – "Instruments for Surgery and Micro Surgery", 1971 Edition, Holco Instruments Corp., 101 Fifth Ave., N.Y., N.Y., 10003; p. 86.
*Knee Joint Retractor for Resections and Arthroplastics,* Levinthal, Daniel, in J. B. & D. Surg. 1931, pp. 378–379.

*Primary Examiner*—Robert W. Michell
*Assistant Examiner*—Arthur S. Rose
*Attorney, Agent, or Firm*—Robert Charles Hill

[57] ABSTRACT

An internal mammary artery sternal retractor suitable for use in human surgery is provided with a handle, an intermediate member which extends upwardly from the handle, a rake which extends perpendicular from the intermediate member and terminates in at least one curved tine, and a heel on the intermediate member which is positioned perpendicular to the intermediate member.

8 Claims, 6 Drawing Figures

INTERNAL MAMMARY ARTERY STERNAL RETRACTOR

BACKGROUND OF THE INVENTION

An internal mammary artery sternal retractor fits over the split edge of a sternum and can be used to lift the sternum to visualize the internal mammary artery which is fixed to the underside thereof.

SUMMARY OF THE INVENTION

Diseases of the heart and large blood vessels are a major medical problem in the United States and throughout many various other parts of the world. In the United States, it is currently estimated that one out of every four individuals in the age group of 45 to 64 years is afflicted with heart or major blood vessel disease to the extent of causing disability, pain, or possible death.

The most common form of heart disease is disease of the coronary arteries produced by arteriosclerosis or hardening of the arteries. The hardened artery becomes like a rigid pipe and the blood cannot flow easily since this pipe is blocked by deposits of cholesterol or calcium. These blocks are called atheromatous plaque.

The heart needs oxygen-rich blood in order to function normally. Since blood cannot flow through the blocked coronary arteries, the heart muscle starves for oxygen-rich blood which causes a person to feel pain over his chest, or angina pectoris. If the heart muscle is starved too long, the muscle fibers die resulting in a heart attack.

Over the years many things have been tried to increase the blood supply to the heart mucscle such as weight reduction and dieting, special drugs, like coronary vasodilators and propranolol, discontinuation of cigarette smoking and a well-supervised excercise program. However, none of these types of treatment or medical programs can prevent a heart attack or the development of further obstruction in the coronary arteries. The only hope is to permanently remove these obstructions or surgically bypass each one.

An operation called endarterectomy removes the blockage in obstructed vessels with the hope that the whole vessel will remain open. However, this operation is not always successful, since the artery may become blocked again because the disease is diffuse in the coronary artery.

In recent years surgical restoration of the coronary circulation has been developed. This type of surgery is referred to as coronary bypass surgery which, in it usual form, directs a new source of blood to the coronary arteries beyond their points of obstruction.

One type of coronary bypass surgery uses an extra or saphenous vein which is carefully removed from the leg and is not needed for normal venous flow therefrom. The vein used for the graft is first anastomosed or attached to the coronary artery beyond its obstruction, with the opposite end connected to the aorta, to form what looks like a new coronary artery. This procedure which has become known as an aortocoronary bypass supplies oxygen-rich blood to the area beyond the obstruction.

A newly developed form of coronary bypass surgery, and the surgery to which the present invention relates, utilizes the internal mammary artery instead of a leg vein to bypass the coronary artery obstruction. This surgical procedure has many advantages over the use of the saphenous vein. First, since the internal mammary artery is located near the heart, only one incision is required and any incision into the leg is completely eliminated, thus reducing the stress exerted on the patient. Second, the internal mammary artery is more similar to the coronary arteries in structure than is a vein. In this procedure one artery does the work of another artery, in contrast to having a vein function as an artery. Third, the internal mammary artery is already connected to the aorta through the subclavian artery so it is only necessary to attach this artery to the coronary artery beyond the obstruction.

In surgical procedures where the internal mammary artery is not used, the sternum is cut vertically in half. The split sternum is maintained in a spaced apart relationship during the operation by suitable equipment well-known in the art.

However, to visualize one or both of the internal mammary arteries which run vertically from the neck toward the abdomen in the chest, it is necessary to lift the split sternum upwardly about the costo-chondral junction which is the movable connection between the sternum and the ribs. The present invention accomplishes this by fitting over the split edge of the sternum so that the sternum can be maintained in a relatively upright position during the internal mammary artery isolation with the heel of the retractor superjacent to costo-chondral junction.

It is the primary object of the present invention to provide a new and improved internal mammary artery sternal retractor.

Another object is to provide a retractor having a rake which fits over the split end of the sternum and a heel which is positioned over the costo-chondral junction.

A further object of the invention is to provide structure of the character described which is economical to produce and long lasting in usage.

DESCRIPTION OF THE PREFERRED EMBODIMENT

Figure 1:
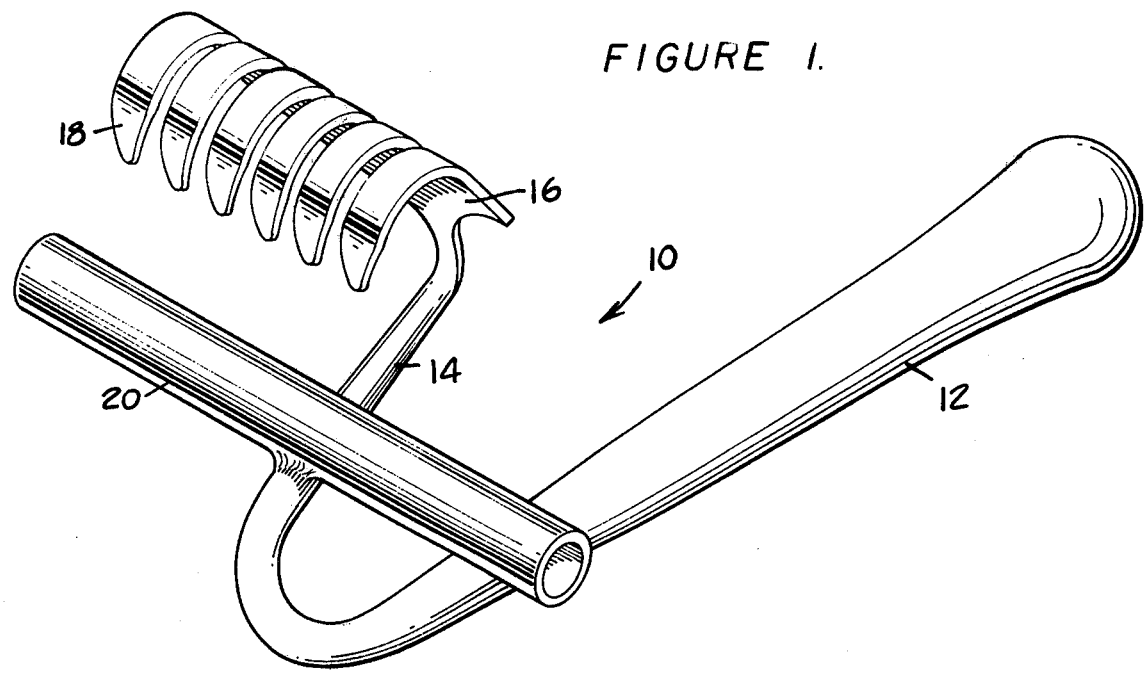
FIG. 1 is a perspective view of the internal mammary artery sternal retractor of the present invention.
Figure 3:
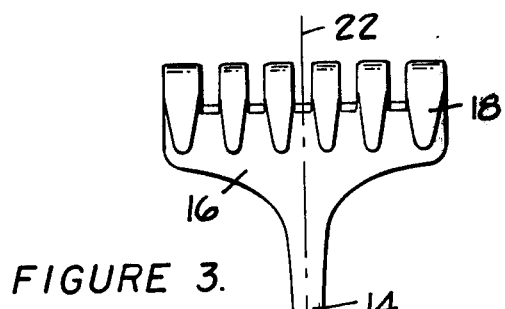
FIG. 3 is a front view of the internal mammary artery sternal retractor.
Figure 2:
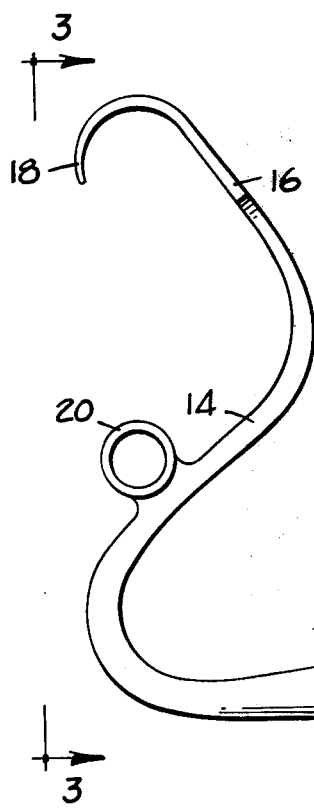
FIG. 2 is a side view of the internal mammary artery sternal retractor.
Figure 2:
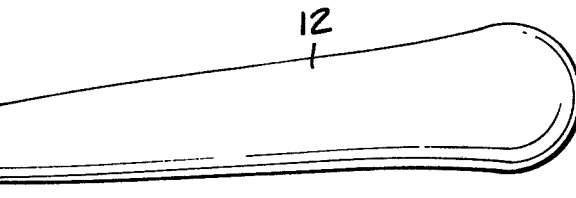

Referring to FIGS. 1 through 3 of the drawings, there is shown the internal mammary artery sternal retractor of this invention, generally indicated 10, which is adaptable for use in human surgery. The internal mammary artery sternal retractor 10 has a handle 12 and an intermediate member 14 extending upwardly therefrom. A rake 16 extends perpendicular from the intermediate member 14 and terminates in at least one curved tine 18. Heel 20 is on intermediate member 14 positioned perpendicular thereto and can be tubular in shape for reasons explained hereafter.

The retractor 10 should be constructed of a lightweight durable material which is easily and quickly sterilized, such as stainless steel or some other metal alloy or a rigid plastic. To reduce the weight of the retractor 10, both the handle 12 and heel 20 can be hollow on the inside. To prevent any unnecessary contamination in hard to reach areas, the ends of the heel 20 may be closed, if desired.

As seen in FIG. 3, the retractor 10 is symmetrical in shape with both the rake 16 and heel 20 approximately equidistant the common vertical center line 22 of the handle 12 and intermediate member 14 and extending perpendicular thereto, even through the length of the heel 20 is greater than the width of the rake 16. As seen in FIG. 2, the retractor 10 is somewhat "swan-like" in shape with the tines 18 curved toward the heel 20 and the intermediate member 14 extending upwardly from the handle 12 at an angle of about 45°. Although the intermediate member 14 is curved as it joins the handle 12 on the bottom portion and leads into the rake 16 on the upper portion, it should be understood that these transition sections could also be at or close to right angles, if desired.

Figure 4:
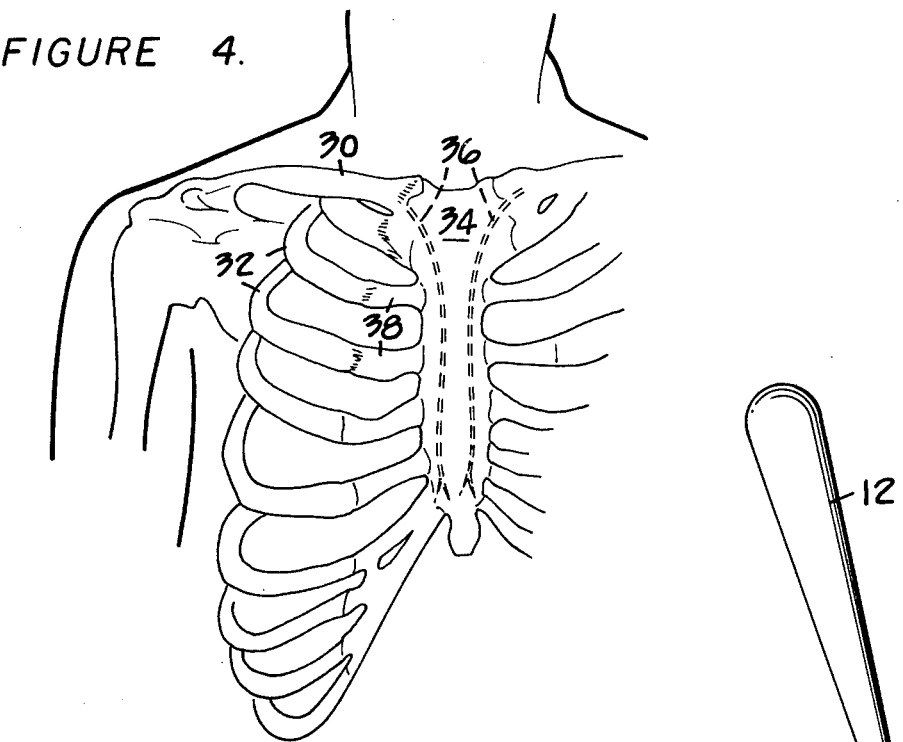
FIG. 4 is a front view of a portion of the human body showing the internal mammary arteries in dotted lines.
Figure 5:
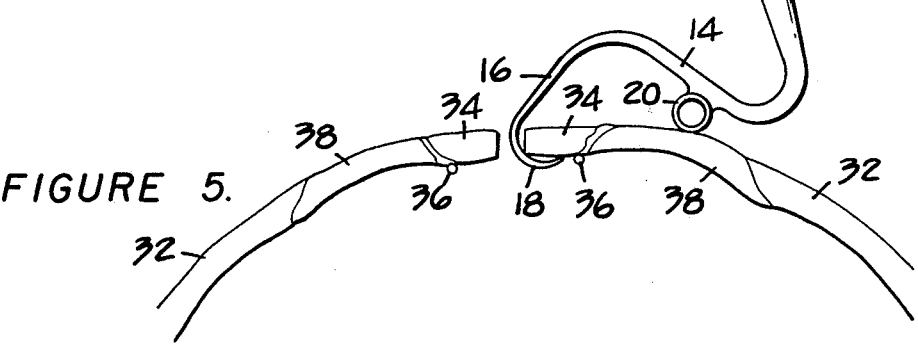
FIG. 5 is an interior sagittal view of a split sternum showing the retractor positioned thereon.
Figure 6:
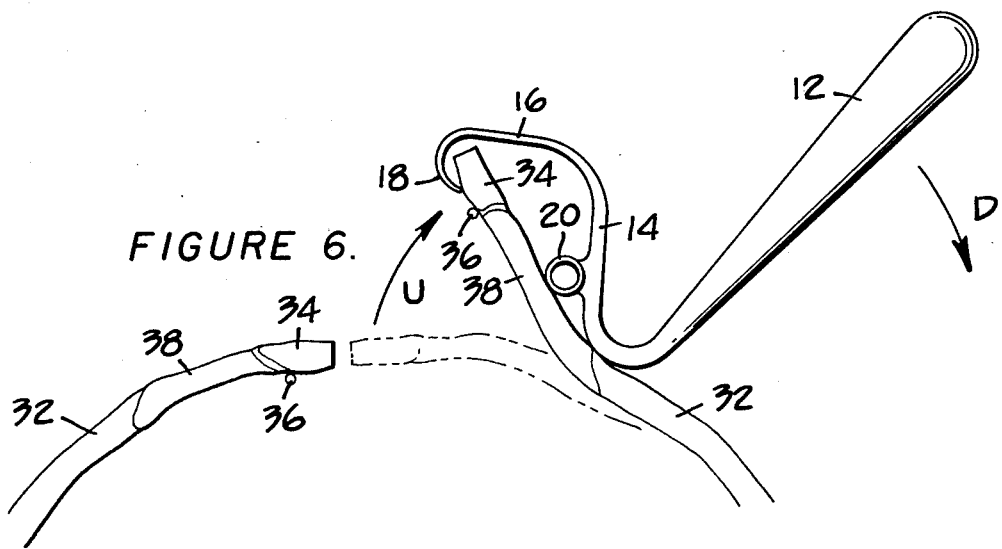
FIG. 6 is a view similar to FIG. 5 showing the split sternum in a relatively upright position.

A typical usage of the internal mammary artery sternal retractor 10 is shown in FIGS. 4 through 6 wherein the human body has a clavicle 30, ribs 32, a sternum 34, and two internal mammary arteries 36 attached to the underside of the sternum 34. After the sternum 34 has been cut vertically in half by a suitable instrument, the tines 18 of the retractor 10 are placed over and around the edge of the split sternum 34 (FIG. 5) with the heel 20 thus positioned over the costro-chondral junction 38 which is the cartiledge connection holding the rib 32 to the sternum 34. This junction 38 is somewhat flexible in nature and keeps the rib 32 and sternum 34 together as the split sternum 34 is being lifted upwardly (FIG. 6) so that the internal mammary artery 36 can be visualized and subsequently operated upon. The shape of the retractor 10 is such that the force needed to lift the split sternum is pivoted about the heel 20 directly above the costro-chondral junction. Downward force D on the handle 12 is transmitted through the retractor 10 into upward movement U of the split sternum 34.

It will be obvious that numerous modifications and variations are possible for the above described internal mammary artery sternal retractor 10 within the scope of the present invention. The foregoing description, as setting forth various constructional and operational details for purposes of understanding only, is not to be taken as limiting the scope of the present invention which is defined only by the following claims.

I claim:

1. An internal mammary artery sternal retractor comprising:
   an elongated, substantially straight handle having two ends,
   an elongated substantially straight intermediate member having first and second ends,
   means for connecting one end of said handle to said first end of said intermediate member such that said handle forms an angle with said intermediate member of from 20° to 60°,
   an elongated substantially straight heel,
   means for connecting said heel to said intermediate member such that said heel is substantially perpendicular to the plane defined by said intermediate member and said handle,
   a substantially flat support member having first and second opposing edges,
   at least one curved tine being connected to said second edge of said support member,
   means for connecting said first edge of said support member to said second end of said intermediate member such that said second edge is further from said handle than said first edge, and said support member is both substantially perpendicular to said intermediate member and substantially parallel to said heel.

2. The internal mammary artery sternal retractor of claim 1 wherein the heel is tubular in shape.

3. The internal mammary artery sternal retractor of claim 2 wherein the heel is a hollow tube.

4. The internal mammary artery sternal retractor of claim 3 wherein the ends of the tube are closed.

5. The internal mammary artery sternal retractor of claim 1 wherein the intermediate member is connected to the heel at about the middle of the heel.

6. The internal mammary artery sternal retractor of claim 1 wherein the tine is curved toward the heel.

7. The internal mammary artery sternal retractor of claim 1 wherein the angle formed between said intermediate member and said handle is about 45°.

8. The internal mammary artery sternal retractor of claim 1 wherein the tine is adapted to fit over a split edge of a patient's sternum and the heel is adapted to fit over a patient's costo-chondral junction.

* * * * *